United States Patent [19]

Bozell et al.

[11] Patent Number: 4,814,489

[45] Date of Patent: Mar. 21, 1989

[54] PROCESS FOR THE PREPARATION OF SUBSTITUTED OLEFINS FROM UNSATURATED ORGANIC CHLORIDES AND OLEFINS

[75] Inventors: Joseph J. Bozell, Ballwin, Mo.; Charles E. Vogt, Waterloo, Ill.

[73] Assignee: Monsanto Company, St. Louis, Mo.

[21] Appl. No.: 77,554

[22] Filed: Jul. 24, 1987

[51] Int. Cl.$^4$ .............................................. C07C 69/76
[52] U.S. Cl. .................................... 560/104; 560/81; 560/55; 558/414; 558/401
[58] Field of Search ........................... 560/104, 81, 55; 558/401, 414

[56] References Cited

FOREIGN PATENT DOCUMENTS 0103544 3/1983 European Pat. Off. .

OTHER PUBLICATIONS

Spencer, A., J. Org. Chem. 270 (1984), 115-120.
Heck et al, J. Orch Chem., vol. 37, No. 14, 1972, pp. 2320-2322.

Primary Examiner—Paul J. Killos
Attorney, Agent, or Firm—Charles E. Smith; James W. Williams, Jr.; Arnold H. Cole

[57] ABSTRACT

A process to prepare a substituted olefin involving reacting an unsaturated organic chloride with bromide and/or iodide ions to form a mixture of unsaturated organic chloride, bromide and/or iodide, and reacting the mixture with an olefin in the presence of a catalyst to form the substituted olefin.

14 Claims, No Drawings

PROCESS FOR THE PREPARATION OF SUBSTITUTED OLEFINS FROM UNSATURATED ORGANIC CHLORIDES AND OLEFINS

FIELD OF THE INVENTION

This invention relates to a catalytic process for the preparation of substituted olefins from unsaturated organic chlorides and olefins.

SUMMARY OF RELATED ART

The palladium catalyzed arylation of olefins is well known in the art as the Heck reaction. The reactivities of aryl halides in the Heck reaction decrease in the order I>Br>Cl>F, i.e., the aryl iodides and aryl bromides are far more reactive than the aryl chlorides and aryl fluorides. Although aryl chlorides are not as reactive, because they are readily available and relatively inexpensive, aryl chlorides are a preferred reactant. The palladium-catalyzed arylation of alkenes with aryl bromides and iodides is reported by T. Mizoroki, K. Mori and A. Ozaki, *Bull. Chem. Soc. Japan*, 1971, 44, 581, and R. F. Heck and J. P. Nolley Jr., *J. Org. Chem.*, 1972, 37, 2320. A. Spencer, *J. Organomet. Chem.*, 1984, 270, 115, discloses the arylation of alkenes with aryl chlorides catalyzed by palladium acetate in the presence of triphenylphosphine. However, only moderate yields with a maximum of 51% are achieved, and the presence of electron withdrawing substituents on the aromatic ring is required to achieve the higher yields. Chlorobenzene undergoes reaction in only 4% yield. J. B. Davison, N. M. Simon and S. A. Sojka, *J. Mol. Catal.*, 1984, 22, 349, disclose the arylation of styrene with chlorobenzene to form stilbene catalyzed by palladium and a sodium or potassium acetate base. Once again, only moderate yields of about 56% and 53% are achieved. European Pat. No. 0,103,544, "Process for Pd-Catalyzed Arylation of Olefins with Aryl Chlorides", discloses the reaction of chlorobenzenes with an olefin in the presence of a base, a palladium catalyst and optionally an arsenic or palladium ligand. Yields of up to 61% are observed for substituted chlorobenzenes, however, a yield of only 4% is observed for chlorobenzene.

The halogen exchange reaction of aromatic bromides with iodide ion in the presence of copper(I) iodide in hot hexamethylphosphoric triamide to give the corresponding iodides is disclosed by H. Suzuki, A. Kondo and T. Ogawa, *Chem. Lett.*, 1985, 411. The halogen exchange of aryl bromides with iodide ion in the presence of a nickel(0) catalyst generated in situ is disclosed by K. Takagi, N. Hayama and S. Inokawa, *Bull. Chem. Soc. Japan*, 1980, 53, 3691. The halogen exchange of aryl bromides and chlorides with iodide ion in the presence of a $NiBr_2$-$Zn$ catalyst is disclosed by K. Takagi, N. Hayama and T. Okamoto, *Chem. Lett.*, 1978, 191.

We have found that unsaturated organic chlorides undergo reaction with olefins to form substituted olefins in relatively high yields by reacting the unsaturated organic chloride with an iodide and/or bromide ion to form a mixture of unsaturated organic chloride, bromide and/or iodide, then performing the Heck reaction, i.e., reacting the resulting mixture with an olefin in the presence of a catalyst.

More specifically, we have found that chlorobenzene reacts with ethyl acrylate to form ethyl cinnamate in relatively high yield by reacting the chlorobenzene with iodide and/or bromide ion to form a mixture of chlorobenzene, iodobenzene and/or bromobenzene, then reacting the mixture with ethyl acrylate in the presence of a catalyst to form ethyl cinnamate.

None of the above references disclose the halogen exchange reaction prior to the Heck reaction to enhance the yield of substituted olefins.

SUMMARY OF THE INVENTION

We have discovered a catalytic process for the preparation of substituted olefins from unsaturated organic chlorides and olefins. The process involves reacting an unsaturated organic chloride with bromide or iodide ion to form a mixture of organic chloride, organic bromide and/or organic iodide, and reacting the mixture with an olefin having at least one hydrogen attached to one of the olefinic carbon atoms, in the presence of a catalyst to form the substituted olefin. The catalyst is a Group VIII metal with an optional phosphine or arsenic ligand.

DETAILED DESCRIPTION OF THE INVENTION

The process of the present invention involves two reactions. The first reaction involves reacting an unsaturated organic chloride with a bromide and/or iodide ion to form a mixture of organic chloride, organic bromide and/or organic iodide. This is effected by an excess of iodide or bromide in the presence of a catalyst as follows:

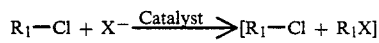

where $R_1$ is an organic radical, $X^-$ is $Br^-$ or $I^-$, and $R_1$—Cl+$R_1$—X is a mixture of unsaturated organic chloride, bromide and/or iodide.

The second reaction of the process involves reacting the mixture with an olefin as follows:

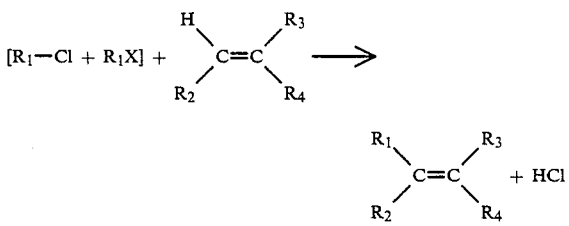

where $R_2$, $R_3$ and $R_4$ are hydrogen or a saturated or unsaturated hydrocarbon, aldehyde, ketone, carboxylic acid, ester, ether or nitrile radical.

The process can be carried out as a one-step process, however, higher yields are obtained when the reactions are performed separately.

THE HALOGEN EXCHANGE REACTION

Any process known in the art for the halogen exchange of organic chlorides with bromide and/or iodide ions is suitable for the present invention. Typically, such processes involve the exchange of the chloride of an unsaturated organic chloride for a bromide or iodide ion in the presence of a catalyst and an excess of bromide or iodide ions.

Organic chlorides suitable for use in the present invention include unsaturated chlorinated hydrocarbons, with or without further substitution. Examples of organic chlorides suitable for the present invention are chlorobenzene, 4-carbomethoxychlorobenzene, methyl-p-chlorobenzoate, 4-chlorobenzonitrile, o-chlorobenzoic acid, 4-chloroanisole, 4-chloroacetophenone, p-chlorophenol, 3-chloropyridine, benzyl chloride, 2-chloronaphthalene, p-methoxybenzyl chloride, vinyl chloride, chloroacetylene, 1-chlorostyrene, 2-chloropropene, 1-chlorocyclohexene, methyl-3-chloroacrylate, 3-chlorobenzaldehyde, chlorophenanthrene, 3-chloro-3-hexene, 1-chlorohexyne, m-chloroaniline, 1,4-dichlorobenzene, chlorofuran and chloro-N-methyl pyrrole.

Any catalyst that will enhance the halogen exchange is suitable for use in the present invention. The preferred catalyst for the halogen exchange is a nickel catalyst. The nickel catalyst can be any form of nickel catalyst, such as nickel metal, nickel complexes, and mixtures of catalysts and halogen sources such as sodium or potassium iodide or bromide. Examples of nickel(0) catalysts include tetrakis(triphenylphosphine)nickel(0), bis(cyclooctadiene) nickel(0), bis(triphenylphosphine)nickeldicarbonyl and bis(triphenylphosphite)nickeldicarbonyl. The preferred nickel catalyst is in the two plus oxidation state. Examples of such nickel catalysts include nickel bromide, and a mixture of nickel bromide and sodium iodide, bis(triphenylphosphine)nickel dibromide, and bis(triphenylphosphine)(phenyl)nickelchloride. A most preferred nickel catalyst is the mixture of nickel bromide and sodium iodide. The mixture is in the range of 20:1 to 1:1 moles of halogen source to moles of nickel catalyst. With respect to the organic chloride, the concentration of nickel catalyst in the halide exchange can vary widely, in the range of about 1:1 to 100:1 moles of organic chloride to moles of nickel catalyst. A preferred range is from 2:1 to 10:1 moles of organic chloride to moles of nickel catalyst.

The halogen exchange reaction of bromide and/or iodide ions occurs in the presence of the nickel catalyst. Preferably there is an excess of bromide or iodide ions. At less than a stoichiometric amount of bromide or iodide, the yield of substituted olefins is reduced. Suitable sources of bromide or iodide ions include salts such as potassium bromide, cesium iodide, lithium bromide, sodium iodide, calcium bromide, and tetraalkylammonium salts of iodide or bromide and mixtures thereof.

The halogen exchange takes place in solution, in a slurry or neat. A preferred exchange reaction is a mixture of the unsaturated organic chloride, nickel catalyst, bromide or iodide ions and a polar organic solvent that is inert to the reactants and has a sufficiently high boiling point to sustain the reaction and not boil. Suitable polar organic solvents include N-methylpyrrolidione, N-methylformamide and dimethyl formamide (DMF). A preferred solvent is DMF. Solvents with lower boiling points may be used in pressurized systems to achieve the required reaction temperature.

The reaction temperature is any temperature sufficient to sustain the reaction. A suitable reaction temperature is in the range of about 100° C. to 175° C. A preferred reaction temperature range is from about 130° C. to about 160° C.

The halogen exchange reaction is not a quantitative exchange of chloride for bromide or iodide. Gas chromatographic analysis of the exchange reaction mass indicates a mixture or complex of unsaturated organic chloride, organic bromide and/or organic iodide. It is theorized that a complex may be formed that activates the organic chloride to undergo the halogen exchange reaction.

THE HECK REACTION

The second reaction of the present invention involves the Heck reaction wherein the mixture of organic chloride, organic bromide and/or organic iodide reacts with an olefin in the presence of a catalyst. The Heck reaction is disclosed in U.S. Pat. Nos. 3,413,352, 3,574,777, 3,527,794, 3,700,727, 3,705,919, 3,763,213, 3,783,140, 3,922,299 and 3,988,358 which are hereby incorporated by reference. The catalyst suitable for the Heck reaction is a Group VIII metal, a preferred group being palladium, nickel and rhodium. A most preferred metal catalyst is palladium. Examples of suitable palladium catalysts include palladium diacetate, tetrakis(triphenylphosphine) palladium(0) and palladium dibenzylideneacetone. The preferred palladium catalyst is palladium dibenzylideneacetone. The catalyst concentration is not critical and can vary widely depending on reaction conditions. The concentration of the catalyst is in the range of 0.01 to 1.0 mole % based on the unsaturated organic chloride. The preferred range is 0.05 to 0.2 mole % based on the unsaturated organic chloride.

Optionally, a trivalent phosphorus or arsenic ligand can be used with the Group VIII metal catalyst. A trivalent phosphorus or arsenic ligand suitable for the present invention is the trialkyl, triaryl, trialkoxy, halo or triphenoxy derivative of phosphorus or arsenic or mixtures thereof. Examples of these ligands are triphenylphosphine, tri-n-butylphosphine, diphenylmethylphosphine, diphenylmethoxyphosphine, tri-methylphosphite, triethylphosphine, phenyldi-n-butoxyphosphine, phosphorus trichloride, phenyldichlorophosphine, arsenic tribromide, triphenylarsine and triphenyl arsenite. The ratio of the ligand to the metal catalyst is not critical. The ratio can vary in the range of about 0.5:1 to about 10:1 mole ratio of ligand to metal catalyst.

The olefin suitable for the present invention contains at least one hydrogen atom bonded to one of the olefinic carbon atoms. The olefin can be selected from unsaturated hydrocarbons, aldehydes, ketones, carboxylic acids and the corresponding nitriles and esters of such acids. Examples of such olefins include cyclic compounds such as cyclohexene, camphene, cyclopentene and indene, vinylic compounds such as divinylbenzene, styrene, ethyl acrylate and acrylonitrile, aryl compounds such as benzene and allylically substituted compounds such as allylbenzene, heterocyclics such as furan and purine and benzylics such as benzylamine.

The Heck reaction takes place in solution, in a slurry or neat. A preferred Heck reaction can be carried out using the unsaturated organic chloride, bromide and/or iodide mixture, a palladium catalyst, a phosphorus or arsenic ligand and a polar organic solvent that is inert to the reactants and has a sufficiently high boiling point to sustain the reaction and not boil. Suitable polar organic solvents include N-methylpyrrolidione, N-methylformamide and dimethyl formamide (DMF). A preferred solvent is DMF. Solvents with lower boiling points may be used in pressurized systems to achieve the required reaction temperature.

The reaction temperature is any temperature sufficient to sustain the reaction and is in the range of about 100° C. to 175° C. A preferred reaction temperature range is from about 130° C. to about 160° C.

The Heck reaction can optionally take place in the presence of a base to absorb the acid generated in the reaction. Suitable bases are weak organic bases that are inert to the reactants. Examples of such bases include trialkyl amines such as triethyl amine and tributyl amine and other organic bases such as sodium acetate, sodium bicarbonate and potassium bicarbonate. A preferred base is triethyl amine.

When chlorobenzene is treated with ethyl acrylate to form ethyl cinnamate, it is preferred that the halogen exchange reaction be catalyzed with a nickel catalyst in the presence of bromide or iodide ions and that the Heck reaction be catalyzed with a palladium catalyst in the presence of a phosphorus or arsenic ligand.

The following examples are for illustrative purposes only and are not intended to limit the scope of the invention in any manner.

EXAMPLES

Analytical Methods

Nuclear magnetic resonance spectra ($^1H$) were measured at 90 mHz on a Varian EM-390 spectrometer or at 300 mHz on a Varian VXR-300 spectrometer using tetramethylsilane as an internal standard and are reported in $\delta$. Infrared spectra were measured on an IBM IR30 instrument and are reported in $cm^{-1}$. Gas chromatographic analysis was performed on a Hewlett-Packard 5790A instrument using an 0.5 mm $\times$ 10 m fused silica capillary columnn. Radial chromatography was performed on a Harrison Research chromatotron using silica gel and a variety of solvent systems. All melting points are uncorrected.

Reagents

The following materials were dried overnight in a vacuum oven at 90° C. and stored under $N_2$ in a dessicator: $NiBr_2$ (Aldrich anhydrous 99.9%) NaI (Fisher), KI (Fisher), $NiCl_2$ (Alfa, ultrapure). tetra(n-butyl)ammonium iodide (n-$Bu_4N^+I^-$) was recrystallized from 95% ethanol and dried at 50° C. in a vacuum oven. Triethylamine was heated for 4 h. over calcium hydride and distilled. Chlorobenzene and dimethylformamide (DMF) were purchased from Aldrich and were used without further purification. Bis(triphenylphosphine)(phenyl)nickelchloride was prepared by the method given in M. Hidai, T. Kashiwagi, T. Ikewchi, Y. Ychida, *J. Organomet. Chem.*, 1971, 30, 279. All other materials were commercially available and used as received. All glassware was dried overnight in a 140° C. oven and assembled while hot under flow of argon.

EXAMPLE 1

Method A

Ethyl cinnamate was prepared as follows:

Chlorobenzene (1130 mg, 10 mmoles, 1.090 ml) $NiBr_2$ (438 mg, 2 mmoles) and NaI (1650 mg, 11 mmoles) were placed in a dry, degassed, airtight flask and were slurried in DMF (20 ml). The mixture was placed in a 140° C. oil bath for 4 to 5 h during which time it darkened to blue-green or deep red. The solution was cooled to room temperature and ethyl acrylate (1100 mg, 11 mmoles, 1.190 ml), triethylamine ($Et_3N$) (1111 mg, 11 mmoles, 1.530 ml), tri-o-tolyl phosphine (P(otol)$_3$) (1216 mg, 4 mmoles) and palladium dibenzylideneacetone (Pd(dba)$_2$) (29 mg, 0.05 mmoles) were added. A cold finger condenser was affixed under a slow argon flow. The mixture was heated overnight in a 140° C. oil bath, typically 15 to 17 h. The mixture was cooled and mixed with about 100 ml diethyl ether ($Et_2O$) to precipitate inorganic salts. If the mixture was to be analyzed by gas chromatography (GC) undecane (0.700 ml) was added as an internal standard. The coupling product was isolated by filtering the $Et_2O$ slurry through a 2"$\times$2"(5.08 cm$\times$5.08 cm) silica gel bed packed in a fritted funnel. The crude material was eluted with an additional 200 to 250 ml $Et_2O$. The combined $Et_2O$ fractions were washed three times with 15 ml aqueous saturated NaCl solutions, dried over $MgSO_4$, filtered and the solvent removed on the rotary evaporator. Radial chromatography (silica gel, 5:1 volume mixture of hexane and $Et_2O$) afforded 1120 mg (65 mole % yield) of ethyl cinnamate as a yellow oil.

Method B

Method B is identical to Method A, except that the phosphine was added at the same time as the $NiBr_2$, chlorobenzene and NaI. The reaction results were essentially the same as those for Method A.

EXAMPLE 2

4-cyano ethyl cinnamate was prepared as follows:

4-Chlorobenzonitrile (1578 mg, 11 mmoles, $NiBr_2$ (438 mg, 2 mmoles) and NaI (1650 mg, 11 mmoles) were combined as described in Method A and treated with ethyl acrylate (1100 mg, 11 mmoles, 1.190 ml), $Et_3N$ (1111 mg, 11 mmoles, 1.530 ml), P(otol)$_3$ (1216 mg, 4 mmoles) and Pd(dba)$_2$ (29 mg, 0.05 mmoles). Isolation by radial chromatography (5:1 volume mixture hexane and $Et_2O$ for the first fraction, 1:1 volume mixture of hexane and $Et_2O$ for the product) gave 1879 mg (93 mole % yield) of 4-cyano ethyl cinnamate as a light brown solid. Recrystallization from a 30:1 volume mixture of hexane and $Et_2O$ gave 1724 mg (85 more % yield) of pure material. The results of, NMR (CDCl$_3$) analysis were: $\delta$1,373 (t,3H,COOCH$_2$CH$_3$), 4.31 (q,2H,COOCH$_2$CH$_3$), 6.53 (d, 1H,PhCH=CH—), 7.6–7.7 (M,5H, aromatic and —CH=CHR), indicating the desired product.

EXAMPLE 3

4-(2-carboethoxyethenyl)-acetophenone was prepared as follows:

4-Chloroacetophenone (1550 mg, 10 mmoles), $NiBr_2$ (438 mg, 2 mmoles) and NaI (1650 mg, 11 mmoles) were mixed according to Method A and treated with ethyl acrylate (1100 mg, 11 mmoles, 1.190 ml), $Et_3N$ (1111 mg, 11 mmoles, 1.530 ml), P(o-tol)$_3$, (1216 mg, 4 mmoles) and Pd(dba)$_2$ (29 mg, 0.05 mmoles). Isolation by radial chromatography as described in Example 2 gave a crude material purified by recrystallization in a 30:1 volume mixture of hexane and $Et_2O$ to give 1400 mg (58%) of 4-(2-carboethoxyethenyl)-acetophenone as a light yellow solid. The results of NMR(CDCl$_3$) analysis were: 1.38 (t, 3H, —COOCH$_2$CH$_3$), 2.64 (S, 3H, —COCH$_3$), 4.31 (q, 2H, COOCH$_2$CH$_3$), 6.54 (d, 1H, PhCH=CH—), 7.63 (d, 2H, aromatic), 7.7 (d, 1H, PhCO=CH—), 7.95 (d, 2H, aromatic), indicating the desired product.

EXAMPLE 4

4-carbomethoxy ethyl cinnamate was prepared as follows:

4-Carbomethoxychlorobenzene (1710 mg, 10 mmoles), $NiBr_2$ (438 mg, 2 mmoles) and NaI (1650 mg, 11 mmoles) were combined according to Method A and were treated with ethyl acrylate (1100 mg, 11 mmoles, 1.130 ml), $Et_3N$ (1111 mg, 11 mmoles, 1.530 ml), P(o-tol)$_3$ (1216 mg, 4 mmoles) and Pd(dba)$_2$ (29 mg, 0.05 mmoles). Isolation by radial chromatography as described in Example 2 gave 595 mg (25 mole % yield) of 4-carbomethoxy ethyl cinnamate as an oily solid. The results of NMR (CDCl$_3$) analysis are: δ1.35 (t, 3H, COOCH$_2$CH$_3$), 3.93(s, 3H, COOCH$_3$), 4.28(q, 2H, COOCH$_2$CH$_3$), 6.5(d, 1H, PhCH=CH—), 7.55 (d, 2H, aromatic), 7.7 (d, 1H, PhCH=CH—), 8.0 (d, 2H, aromatic), indicating the desired product.

EXAMPLE 5 4-methoxy ethyl cinnamate was prepared as follows:

4-Chloroanisole (1430 mg, 10 mmoles, 1229 ml), NiBr$_2$ (438 mg, 2 mmoles), NaI (1650 mg, 11 mmoles) and P(o-tol)$_3$ (1216 mg, 4 mmoles) were combined according to Method B and treated with ethyl acrylate (1100 mg, 11 mmoles, 1.130 ml), Et$_3$N (1111 mg, 11 mmoles, 1.530 ml), and Pd(dba)$_2$ (29 mg, 0.05 mmoles). Isolation by radial chromatography as described in Example 2 (Si gel, 5:1 volume mixture of hexane and Et$_2$O for the first fraction, 1:1 volume mixture of hexane and Et$_2$O for the second) gave 1519 mg (74 mole % yield) of 4-methoxy ethyl cinnamate as a brown oil. The results of NMR (CDCl$_3$) analysis were: δ1.35 (t, 3H,— COOCH$_2$CH$_3$), 3.84 (s, 3H, OCH$_3$), 4.26 (q, 2H, COOCH$_2$CH$_3$), 6.33 (d, 1H, PhCH=CH—), 6.90 (d, 2H, aromatic), 7.49 (d, 2H, aromatic), 7.65 (d, 1H, PhCH=CH—R), indicating the desired product.

EXAMPLE 6

Cinnamonitrile was prepared as follows:

Chlorobenzene (1130 mg, 10 mmoles, 1.090 ml), NiBr$_2$ (438 mg, 2 mmoles) NaI (1650 mg, 11 mmoles) and P(o-tol)$_3$ (1216 mg, 4 mmoles) were mixed as described in Method B and were treated with acrylonitrile (583 mg, 11 mmoles, 0.723 ml), Et$_3$N (111 mg, 11 mmoles, 1.530 ml), and Pd(dba)$_2$ (29 mg, 0.05 mmoles). GC analysis indicated that cinnamonitrile was produced in 62% selectivity at 46% conversion, i.e. a yield of about 8%.

Various solvents were evaluated for the organic chloride and bromide and/or iodide ion reaction as follows: Chlorobenzene (1130 mg, 10 mmoles, 1.02 ml), n-Bu$_4$N$^+$I$^-$ (7390 mg, 20 mmoles), NiBr$_2$ (55 mg, 0.25 mmoles) and triphenylphosphine(210 mg, 0.8 mmoles) were mixed as described in Method A in the various solvents indicated below and heated in an oil bath at the temperatures indicated below. GC analysis was performed after heating for about 18 h.

| Solvent | Oil Bath Temperature | Conversion |
| --- | --- | --- |
| Acetone* | 150 | None |
| Acetonitrile* | 150 | None |
| Formamide | 150 | None |
| N—methylpyrrolidione | 150 | 15% |
| Aqueous acetonitrile** | 150 | None |
| N—methylformamide | 150 | 7% |

*The exchange took place in a pressure bottle.
**The acetonitrile/water mixture was 90/10 volume/volume. The iodide source was NaI (4500 mg, 30 mmoles) rather than n-Bu$_4$N$^+$I$^-$, and the phosphine was tributylphosphine (0.2 ml, 0.8 mmoles) rather than triphenylphosphine.

Presumably, the above solvents that were ineffective did not reach a sufficiently high temperature to sustain the halogen exchange.

Various nickel catalysts were evaluated as suitable catalysts for the halogen exchange as follows:

EXAMPLE 7

Nickel bromide was evaluated as an exchange catalyst as follows: Chlorobenzene (1130 mg, 10 mmoles) and NiBr$_2$ (438 mg, 2 mmoles) were placed in a dry, degassed, airtight flask, slurried in DMF (20 ml), and reacted with ethyl acrylate according to method A. After 17 h, the reaction yielded ethyl cinnamate in 75% selectivity at 35% conversion.

CONTROL 1

Nickel bromide in the presence of lithium chloride was evaluated as an exchange catalyst as follows: Chlorobenzene (1130 mg, 10 mmoles), NiBr$_2$ (438 mg, 2 mmoles) and LiCl (462 mg, 11 mmoles) were placed in a dry, degassed, airtight flask, slurried in DMF (20 ml) and reacted with ethyl acrylate according to method A. After 17 h, GC analysis indicated no conversion to ethyl cinnamate.

CONTROL 2

Nickel chloride was evaluated as an exchange catalyst as follows: Chlorobenzene (1130 mg, 10 mmoles), NiCl$_2$ (258 mg, 2 mmoles) and P(o-tol)$_3$ (1216 mg, 4 mmoles) were placed in a dry, degassed, airtight flask, slurried in DMF (20 ml), and reacted with ethyl acrylate according to method B. After 17 h, GC analysis indicated no conversion to ethyl cinnamate.

EXAMPLE 8

Nickel chloride in the presence of sodium iodide was evaluated as an exchange catalyst as follows: Chlorobenzene (1130 mg, 10 mmoles), NiCl$_2$ (258 mg, 2 mmoles), NaI (1650 mg, 11 mmoles) and P(o-tol)$_3$ (1216 mg, 4 mmoles) were placed in a dry, degassed, airtight flask, slurried in DMF (20 ml) and reacted with ethyl acrylate according to method B. After 17 h, GC analysis indicated about 50 % yield of ethyl cinnamate.

CONTROL 3

Nickel acetonylacetate (Ni(acac)$_2$) was evaluated as an exchange catalyst as follows: Chlorobenzene (1130 mg, 10 mmoles), Ni(acac)$_2$ (514 mg, 2 mmoles), NaI (1650 mg, 11 mmoles) and P(o-tol)$_3$ (1216 mg, 4 mmoles) were placed in a dry, degassed, airtight flask, slurried in DMF (20 ml) and reacted with ethyl acrylate according to method B. After 17 h, GC analysis indicated no conversion to ethyl cinnamate.

EXAMPLE 9

Bis(cyclooctadiene)nickel (Ni(cod)$_2$) was evaluated as an exchange catalyst as follows: Chlorobenzene (1130 mg, 10 mmoles), Ni(cod)$_2$ (550 mg, 2 mmoles), NaI (1650 mg, 11 mmoles) and P(o-tol)$_3$ (1216 mg, 4 mmoles) were placed in a dry, degassed airlessware flask, were slurried in DMF (20 ml) and reacted with ethyl acrylate according to method B. After 17 h, GC analysis indicated ethyl cinnamate in 80% selectivity at 20% conversion.

EXAMPLE 10

Bis(triphenylphosphite)dicarbonylnickel ([(PhO)$_3$P]$_2$Ni(CO)$_2$) was evaluated as an exchange catalyst as follows: Chlorobenzene (1130 mg, 10 mmoles), ([(PhO)$_3$P]$_2$Ni(CO)$_2$) (1470 mg, 2 mmoles), NaI (1650 mg, 11 mmoles) and P(o-tol)$_3$ 1216 mg, 4 mmoles) were placed in a dry, degassed, airtight flask, slurried in DMF (20 ml) and reacted with ethyl acrylate according to method B. After 17 h, GC analysis indicated ethyl cinnamate in 27% selectivity at 34% conversion.

EXAMPLE 11

Bis(triphenylphosphine)(phenyl)nickel chloride (Ni complex) was evaluated as an exchange catalyst as follows: Chlorobenzene (433 mg, 383 mmoles), Ni complex (533 mg, 0.77 mmoles), NaI (632 mg, 4.21 mmoles) and P(o-tol)$_3$(468 mg, 1.54 mmoles) were placed in a dry, degassed, airtight flask, were slurried in DMF (20 ml) and reacted with ethyl acrylate according to method B. After 17 h, GC analysis indicated ethyl cinnamate in 5% selectivity at 45% conversion.

Control 4

Nickel bromide in the presence of zinc was evaluated as an exchange catalyst as follows: Chlorobenzene (2825 mg, 25 mmoles), NiBr$_2$ (137 mg, 0.625 mmoles), NaI (4125 mg, 27.5 mmoles), triphenyl phosphine (PPh3) (328 mg, 1.3 mmoles) and zinc metal (85 mg, 1.3 mmoles) were placed in a dry, degassed, airtight flask and were slurried in DMF (20 ml) and stirred at room temperature for 4 h. The mixture was treated with ethyl acrylate (2750 mg, 27.5 mmoles) Et$_3$N (2778 mg, 27.5 mmoles), PPh$_3$ (262 mg, 1 mmole) and palladium diacetate (56 mg, 0.25 mmoles). The mixture was heated for about 12 h at 140° C. After 17 h, GC analysis indicated no conversion to ethyl cinnamate.

CONTROL 5

Bis(triphenylphosphine)nickel dibromide ((PPh$_3$)$_2$NiBr$_2$) was evaluated as an exchange catalyst. Chlorobenzene (2825 mg, 25 mmoles), (PPh$_3$)$_2$NiBr$_2$ (464 mg, 0.625 mmoles) and NaI (4125 mg, 27.5 mmoles) were placed in a dry, degassed, airtight flask and were slurried in DMF (20 ml) and heated at 140° C. for 4 h. The mixture was treated with ethyl acrylate (2750 mg, 27.5 mmoles) Et$_3$N (2778 mg, 27.5 mmoles), PPh$_3$ (262 mg, 1 mmole) and palladium diacetate (56 mg, 0.25 mmoles). The mixture was heated for about 17 h at 140° C. After 17 h, GC analysis indicated no conversion to ethyl cinnamate.

CONTROL 6

Bis(triphenylphosphine)dicarbonylnickel ((PPh$_3$)$_2$Ni(CO)$_2$) was evaluated as an exchange catalyst as follows: Chlorobenzene (2825 mg, 25 mmoles), (PPh$_3$)$_2$Ni(CO)$_2$ (262 mg, 1 mmole), n-Bu$_4$N$^+$I$^-$ (9225 mg, 25 mmoles), PPh$_3$ (262 mg, 1 mmole), ethyl acrylate (2750 mg, 27.5 mmoles), sodium acetate (2255 mg, 27.5 mmoles) and palladium diacetate (56 mg, 0.25 mmoles) were placed in a dry, degassed airtight flask, slurried in DMF (20 ml) and heated for 8 h at 140° C. The catalyst decomposed under these conditions and no ethyl cinnamate was observed.

EXAMPLE 12

Tetrakis(triphenylphosphine)nickel(0) (Ni(PPh$_3$)$_4$) was evaluated as an exchange catalyst as follows: Chlorobenzene (2454 mg, 21.75 mmoles), Ni(PPh$_3$)$_4$ (602 mg, 0.625 mmoles) and NaI (3583 mg, 23.9 mmoles) were placed in a dry, degassed airtight flask, slurried in DMF (20 ml) and heated at 140° C. for 4 h. In a separate airtight flask were mixed ethyl acrylate (2750 mg, 27.5 mmoles), Et$_3$N (2778 mg, 27.5 mmoles), PPh$_3$ (262 mg, 1 mmole) and palladium diacetate (56 mg, 0.25 mmoles). The nickel mixture and the palladium mixture were combined in a degassed pressure bottle via needlestock. The bottle was capped and heated to 140° C. for about 17 h. After 17 h., GC analysis indicated a low conversion and selectivity to ethyl cinnamate (<5%).

The sources of palladium catalyst and phosphine ligand were varied as follows:

EXAMPLE 13

Bis(diphenylphosphino)ethane (DIPHOS) was used as the phosphine ligand and palladium diacetate was used as the palladium catalyst as follows: NiBr$_2$(137 mg, 0.625 mmoles), DIPHOS (249 mg, 0.625 mmoles) and Zn metal (122 mg, 0.875 mmoles) were combined in an airtight flask in DMF (5 ml) and stirred at about 23° C. for 1 h. In a separate pressure vessel were mixed chlorobenzene (2825 mg, 25 mmoles), n-Bu$_4$N$^+$I$^-$ (9225 mg, 25 mmoles), ethyl acrylate (2750 mg, 27.5 mmoles), sodium acetate (2255 mg, 27.5 mmoles) and palladium diacetate (56 mg, 0.25 mmoles) in DMF (20 ml). The nickel mixture was added to the palladium mixture via needlestock and the resulting mixture stirred in a 145° C. oil bath for 8 h. GC analysis indicated a conversion of less than 5% to ethyl cinnamate.

EXAMPLE 14

Triphenylphosphine (PPh$_3$) was used as the phosphine ligand and tetrakis(triphenylphosphine)palladium (Pd(PPh$_3$)$_4$) was used as the palladium catalyst as follows: Chlorobenzene (2825 mg, 25 mmoles), NiBr$_2$ (1095 mg, 5 mmoles), NaI(4125 mg, 27.5 mmoles) and PPh$_3$ (2620 mg, 10 mmoles) were mixed in DMF 20 ml) and heated in 140° C. oil bath for 5 h. The mixture was cooled and treated with ethyl aorylate (2750 mg, 27.5 mmoles), Et$_3$N (2778 mg, 27.5 mmoles), and Pd(PPh$_3$)$_4$ (800 mg, 0.692 mmoles). The mixture was heated in a 140° C. oil bath for 18 h. The crude reaction mixture was mixed with Et$_2$O, filtered and washed once with 10 ml of saturated NaCl. The solvent was removed on the rotary evaporator and the residue purified by radial chromatography (5:1 volume mixture of hexane and Et$_2$O) to give 1540 mg (34% isolated yield) of ethyl cinnamate as a light yellow oil.

EXAMPLE 15

PPh$_3$ was used as the phosphine ligand and palladium diacetate was used as the palladium catalyst as follows:

Chlorobenzene (2825 mg, 25 mmoles), NiBr$_2$ (1095 mg, 5 mmoles), NaI(4125 mg, 27.5 mmoles) and PPh$_3$ (2620 mg, 10 mmoles) were mixed in DMF (20 ml) and heated in 40° C. oil bath for 5 h. The mixture was cooled and treated with ethyl acrylate (2750 mg, 27.5 mmoles), Et$_3$N (2778 mg, 27.5 mmoles), palladium diacetate (56 mg, 0.25 mmoles), and PPh$_3$ (262 mg, 1 mmole). The mixture was heated in a 140° C. oil bath for 18 h. The crude reaction mixture was mixed with Et$_2$O, filtered and washed three times with 50 ml of water. The organic fraction was dried over MgSO$_4$, the solvent was removed on the rotary evaporator and the residue purified by radial chromatography (5:1 volume mixture of hexane and Et$_2$O, two purifications) to give 1700 mg (39% isolated yield) of ethyl cinnamate as a light yellow oil.

We claim:

1. A process of preparing a substituted olefin comprising reacting an unsaturated organic chloride with bromide and/or iodide ions to form a mixture of unsaturated organic chloride, organic bromide and/or organic iodide, and reacting the mixture with an olefin having at least one hydrogen attached to one of the olefinic carbon atoms in the presence of a catalyst to form the substituted olefin.

2. The process of claim 1 wherein the reaction of the unsaturated organic chloride is catalyzed by a nickel catalyst in the presence of bromide or iodide ions.

3. The process of claim 2 wherein the bromide and/or iodide ions are provided by a salt selected from the group consisting of potassium bromide, cesium iodide, lithium bromide, sodium iodide, calcium bromide and tetraalkylammonium salts of iodide or bromide or mixtures thereof.

4. The process of claim 3 wherein the nickel catalyst is nickel bromide and the iodide ion is provided by an excess of sodium iodide.

5. The process of claim 4 wherein the unsaturated organic chloride is a substituted or unsubstituted chlorobenzene and the olefin is selected from ethyl acrylate and acrylonitrile.

6. The process of claim 1 wherein the catalyst is a Group VIII metal.

7. The process of claim 6 wherein the catalyst is selected from the group consisting of palladium, nickel and rhodium.

8. The process of claim 7 wherein the catalyst is a palladium catalyst selected from the group consisting of palladium diacetate, tetrakis(triphenylphosphine)palladium(0) and palladium dibenzylideneacetone.

9. The process of claim 8 wherein present with the catalyst is a trivalent phosphorus or arsenic ligand.

10. The process of claim 9 wherein the phosphorus ligand is selected from the group consisting of triphenyl phosphine, bis(diphenylphosphino)ethane and tri-o-tolyl phosphine.

11. The process of claim 10 wherein the catalyst is palladium dibenzylideneacetone with tri-o-tolyl phosphine.

12. A process to prepare ethyl cinnamate comprising reacting a substituted or unsubstituted chlorobenzene with a bromide and/or iodide ion to form a mixture of the chlorobenzene, a bromobenzene and/or a iodobenzene and reacting the mixture with ethyl acrylate in the presence of a palladium catalyst and a phosphine ligand to form the ethyl cinnamate.

13. The process of claim 12 wherein the chlorobenzene is unsubstituted and the chlorobenzene reaction is catalyzed by nickel bromide in the presence of sodium iodide.

14. The process of claim 13 wherein the palladium catalyst is palladium dibenzylideneacetone with tri-o-tolyl phosphine.

* * * * *